(12) United States Patent
Mackay

(10) Patent No.: US 9,745,564 B2
(45) Date of Patent: Aug. 29, 2017

(54) ENZYME SYSTEM FOR EXTRACTION OF PROTEINS FROM DISTILLERS GRAINS

(71) Applicant: Ian Mackay, Eden Praire, MN (US)

(72) Inventor: Ian Mackay, Eden Praire, MN (US)

(73) Assignee: Zealo, Eden Praire, MN (US)

(*) Notice: Subject to any disclaimer, the term of this patent is extended or adjusted under 35 U.S.C. 154(b) by 109 days.

(21) Appl. No.: 14/605,931

(22) Filed: Jan. 26, 2015

(65) Prior Publication Data
US 2015/0208688 A1    Jul. 30, 2015

Related U.S. Application Data

(60) Provisional application No. 61/931,663, filed on Jan. 26, 2014.

(51) Int. Cl.
| | | |
|---|---|---|
| *A23J 1/00* | (2006.01) | |
| *C12N 9/52* | (2006.01) | |
| *C12N 9/50* | (2006.01) | |
| *A23J 1/12* | (2006.01) | |

(52) U.S. Cl.
CPC ............. *C12N 9/50* (2013.01); *A23J 1/125* (2013.01); *C12Y 304/21* (2013.01)

(58) Field of Classification Search
CPC .. A23J 1/005; A23J 1/006; C12N 9/50; C12N 9/52
See application file for complete search history.

(56) References Cited

U.S. PATENT DOCUMENTS

| | | | |
|---|---|---|---|
| 4,828,846 A * | 5/1989 | Rasco | ............... A21D 2/36 426/18 |
| 7,494,675 B2 | 2/2009 | Abbas | |
| 7,504,245 B2 | 3/2009 | Kinley | |
| 8,257,951 B2 | 9/2012 | Prevost | |
| 9,493,851 B2 | 11/2016 | Jansen | |

OTHER PUBLICATIONS

Celus, I., et al., 2009, "Fractionation and Characterization of Brewers' Spent Grain Protein Hydrolysates", Journal of Agricultural and Food Chemistry, vol. 57, pp. 5563-5570.*
Y.Victor Wu; Protein Concentrate From Normal and High-L-Lysine Corns by Alkaline Extraction; USDA Northern Regional Research Lab, ARS, Peoria, IL.

* cited by examiner

*Primary Examiner* — Maryam Monshipouri
(74) *Attorney, Agent, or Firm* — Henry E. Naylor

(57) ABSTRACT

An enzyme system for the extraction of proteins from distillers grains and roots. The enzyme system is a three component system containing a first component of protease enzyme and a buffer, a second component comprised of a deactivating agent, and a third component comprised of neutralizing agent.

2 Claims, No Drawings

ENZYME SYSTEM FOR EXTRACTION OF PROTEINS FROM DISTILLERS GRAINS

CROSS-REFERENCE TO RELATED APPLICATIONS

This application is based on Provisional Application 61/931,663 filed Jan. 26, 2014.

FIELD OF THE INVENTION

This invention relates to an enzyme system for the extraction of proteins from distillers grains and roots. The enzyme system is a three component system containing a first component of protease enzyme and a buffer, a second component comprised of a deactivating agent, and a third component comprised of neutralizing agent.

BACKGROUND OF THE INVENTION

A lack of sufficient food remains a critical issue in many underdeveloped populations particularly among children. For example, the World Health Organization reports that as many as 30% of the children in Sub Saharan Africa are malnourished. In particular, insufficient protein intake can lead to a condition called Protein Energy Malnutrition that can be fatal if not treated and even if treated, once contracted can lead to both mental and physical long-term developmental deficiencies. Protein malnutrition is detrimental at any point in life, but protein malnutrition prenatally has been shown to have significant lifelong effects. During pregnancy, one should aim for a diet that consists of at least 20% protein for the health of the fetus. Diets that consist of less than 6% protein in utero have been linked with many deficits, including decreased brain weight, increased obesity, impaired communication within the brain. Even diets of mild protein malnutrition have been shown to have lasting and significant effects. Thus, there exists a need for a means to provide low cost supplementary protein to underdeveloped populations.

Many villages in underdeveloped areas of the world utilize local grains and or roots to brew alcoholic beverages. For example, in several countries of Africa, 30% of the total beer production of the continent is made at the village level. The grains and roots used to produce this beer represent an underutilized source of protein available at the local level. During beer production, following an initial steeping process, the grains are typically discarded while the steeped liquor is fermented to produce the beer. The grains can also be used for animal feed and contain up to 30% protein at that point. For purposes of this invention, both the used grains and roots are referred to as distillers grains or roots.

The proteins of the distillers grains or roots are not soluble or easily digested without further treatment. Therefore a process is needed to extract proteins from these grains and roots so they can be used on the village level to enhance the protein diet of the population. The present invention relates to a product and process for extracting protein from distillers grains or roots and forming a high protein broth that can be used to supplement such things as soups, stews and starch dishes thus adding the much needed protein to the local diet.

SUMMARY OF THE INVENTION

In accordance with the present invention there if provided a an enzyme system comprised of three components, wherein a first component is comprised of an effective amount of at least one protease enzyme and an effective amount of a buffer effective for maintaining an aqueous mixture of said first component in a pH range that allows hydrolysis of proteins; a second component is comprised of an effective amount of a deactivating agent, and a third component is comprised of an effective amount of a neutralizing agent.

In one preferred embodiment the protease enzyme is selected from the group consisting of serine proteases, threonine proteases, cysteine proteases, aspartate proteases, glutamic acid proteases, and metalloproteases.

Also in accordance with the present invention there is provided s process for producing a protein-rich broth from distillers grains or roots, which process comprises:

a) providing an aqueous mixture of protein-containing distillers grains or roots;

b) heating said aqueous mixture of protein-containing distillers grains or roots to a temperature from about 100° F. to about 125° F. for an effective amount of time;

c) hydrolyzing proteins of said protein-containing heated aqueous mixture of b) above by adding an effective amount of an enzyme system comprised of a protease enzyme and a buffer capable of maintaining the heated aqueous mixture at a pH effective for the hydrolysis of proteins;

d) stopping the hydrolysis reaction by adding a hydrolysis deactivating agent to the mixture of c) above;

e) adding a neutralizing agent to the mixture of d) above and allowing the mixture to simmer for an effective amount of time to result in a protein-rich broth; and f) draining off and recovering a resulting protein-rich broth.

DETAILED DESCRIPTION OF THE INVENTION

In one preferred embodiment of the present invention the three component system is in powder form. A first component, to which water is added, is comprised of two ingredients, a protease enzyme and a buffer. The protease enzyme is one that is effective for at least partially hydrolyzing the proteins in the distillers grains or roots thus rendering them substantially water-soluble. The buffer, preferably a carbonate, is one that is effective for maintaining the proper pH of a resulting aqueous broth during the hydrolysis reaction. A pH of 8.0 to 8.5 is preferred when the protease enzyme is Alcalase. A second component is comprised of a deactivation agent and a third component is comprised of a neutralizing agent. The deactivation agent is comprised of a material that when added to the aqueous mixture in which proteins are being hydrolyzed will substantially stop the hydrolysis reaction. In a typical embodiment, where Alcalase is the protease enzyme being utilized, the deactivating agemt is a citric acid salt capable of lowering the pH to about 4 to 5,preferably from about 4 to 4.5.The deactivating agent is used to deactivate the enzyme to prevent the formation of bitter peptides that will adversely affect the taste of the protein extraction product. Other food grade acid agents, such as ascorbic acid, can also be used. A third component of the enzyme system of the present invention is a neutralizing agent. The neutralizing component, which preferably contains a phosphate salt, is used to adjust the pH of the resulting protein extract product to about 7.0 to avoid a sour taste in the final protein extract product.

An effective amount of protease enzyme is at least that amount needed to hydrolyze at least about 10%, preferably greater than 30%, and more preferably greater than 50% all of the longer chain proteins in the distillers grains to smaller chain peptides and amino acids. This effective amount will be in the range of about 0.8 to about 1.2 weight percent, preferably about 1 weight percent. The enzyme treated distillers grains are subjected to hydrolysis conditions to cause at least a fraction of the proteins of the distillers grains to hydrolyze, thus resulting in water soluble smaller chain materials, such as peptides and amino acids. The protease enzyme will preferably be used in an aqueous solution form of adequate concentration to provide the 0.8 to 1.2 wt. % based on the weight of distillers grains being treated.

In another embodiment of the present invention, a single component mixture can be used in place of the three component system. In this instance only the component comprised of the protease enzyme and a buffer is used. The protease enzyme is one that is effective for at least partially hydrolyzing the proteins in the distillers grains or roots thus rendering them substantially water-soluble. The buffer, preferably a carbonate, is one that is effective for maintaining the proper pH of a resulting aqueous broth during the hydrolysis reaction. A pH of 8.0 to 8.5 is preferred when the protease is Alcalase. The resulting protein extraction product of the present invention can be packaged as a mixed powder and can be incorporated in a gelatin pack that is designed to break down at the appropriate hydrolysis temperature. In this embodiment, heat may be used to deactivate the enzyme so that a deactivating component and a neutralizing component will not be required.

Proteins are extracted from the distillers grains or roots by adding an effective amount of water to the distillers grains or roots and heating the aqueous mixture to a temperature from about 100° F. to a temperature below which the proteins will start to denature. Preferably this temperature will be from about 100° F. to about 125° F., which is lower than the temperature that is used as the steeping temperature for brewing. The protein extraction product of the present invention is then added to the hot mixture and stirred for an effective amount of time, preferably from about 20 to 60 minutes, more preferably from about 20 to 50 minutes and most preferably from about 25 to 40 minutes. If a deactivation component is to be utilized, it is then mixed in to the broth to halt the hydrolysis process before bitter peptides can be formed. After mixing for up to 5 minutes, the neutralizer component is added and the resulting broth is allowed to simmer until the desired broth consistency is achieved. If the mixture is to be heat deactivated, it can simply be simmered until the desired broth consistency is achieved. The protein-extracted distillers grains or roots are drained off and used for animal feed or dried and used as fuel, or discarded. The resulting broth will be rich in protein, typically from about 40% to about 50% or more protein depending on the consistency desired and is ready for use. The decision on which instance of the invention is most desirable will depend on taste preferences and economic conditions of the user. The first instance is more expensive and results in a more tangy final product whereas the second instance is less expensive but will result in a softer taste.

It will be understood that when the term "distillers grains" are used alone herein the term includes both distillers grains and roots Any suitable protease enzyme can be used in the practice of the present invention. A protease enzyme is one that performs proteolysis, that is, begins protein catabolism by hydrolysis of the peptide bonds that link amino acids together in the polypeptide chain forming the protein. Non-limiting examples of protease enzymes that can be used in the practice of the present invention include serine proteases, threonine proteases, cysteine proteases, aspartate proteases, glutamic acid proteases, and metalloproteases. Serine proteases are preferred.

What is claimed is:

1. An enzyme system in powder form comprised of three components, wherein a first component is comprised of an effective amount of at least one serine protease enzyme and an effective amount of a carbonate buffering agent effective for maintaining an aqueous mixture of said protease enzyme in a pH range that allows hydrolysis of proteins; a second component comprised of an effective amount of a deactivation component selected from the group consisting of citric acid and ascorbic acid, and a third component comprised of an effective amount of a neutralizer component.

2. A process for producing a protein rich broth from distillers grains or roots, which process comprises:
   a) providing an aqueous mixture of protein-containing distillers grains or roots;
   b) heating said aqueous mixture of protein-containing distillers grains or roots to a temperature from about 100° F. to about 125° F. for an effective amount of time;
   c) hydrolyzing proteins of said protein-containing heated aqueous mixture of b) above by adding an effective amount of an enzyme system comprised of a serine protease enzyme and a carbonate buffer capable of maintaining the heated aqueous mixture at a pH effective for the hydrolysis of proteins;
   d) stopping the hydrolysis reaction by adding a deactivating agent selected from the group consisting of citric acid and ascorbic acid to the mixture of c) above;
   e) adding a neutralizer component to the mixture of d) above and allowing the mixture to simmer for an effective amount of time; and
   f) draining off a resulting protein-rich broth.

* * * * *